(12) United States Patent
Xu

(10) Patent No.: US 10,682,074 B2
(45) Date of Patent: Jun. 16, 2020

(54) WOUND MEASUREMENT ON SMART PHONES

(71) Applicant: Dermagenesis LLC, Pompano Beach, FL (US)

(72) Inventor: Tianning Xu, Atlanta, GA (US)

(73) Assignee: DermaGenesis, LLC, Pompano Beach, FL (US)

( * ) Notice: Subject to any disclaimer, the term of this patent is extended or adjusted under 35 U.S.C. 154(b) by 1051 days.

(21) Appl. No.: 14/613,471

(22) Filed: Feb. 4, 2015

(65) Prior Publication Data

US 2015/0150490 A1    Jun. 4, 2015

Related U.S. Application Data

(62) Division of application No. 13/716,532, filed on Dec. 17, 2012.

(60) Provisional application No. 61/705,404, filed on Sep. 25, 2012.

(51) Int. Cl.
| | |
|---|---|
| *A61B 5/107* | (2006.01) |
| *A61B 5/00* | (2006.01) |
| *G06T 7/00* | (2017.01) |
| *H04N 5/44* | (2011.01) |

(52) U.S. Cl.
CPC .......... *A61B 5/1079* (2013.01); *A61B 5/0077* (2013.01); *A61B 5/1072* (2013.01); *A61B 5/445* (2013.01); *A61B 5/6898* (2013.01); *A61B 5/742* (2013.01); *A61B 5/7475* (2013.01); *G06T 7/0012* (2013.01); *H04N 5/44* (2013.01); *A61B 2576/02* (2013.01)

(58) Field of Classification Search
CPC ...... G06T 7/0012; H04N 5/44; A61B 5/1079; A61B 5/0077; A61B 5/7475
See application file for complete search history.

(56) References Cited

U.S. PATENT DOCUMENTS

| | | | |
|---|---|---|---|
| 5,056,934 A | 10/1991 | Ielmini et al. | |
| 5,967,979 A | 10/1999 | Taylor et al. | |
| 6,567,682 B1 * | 5/2003 | Osterweil ............ | A61B 5/0059 348/77 |
| 7,723,560 B2 | 5/2010 | Lockwood et al. | |
| 2007/0276309 A1 * | 11/2007 | Xu .......................... | A61B 5/107 602/52 |
| 2008/0071162 A1 | 3/2008 | Jaeb et al. | |
| 2008/0273755 A1 | 11/2008 | Hildreth | |
| 2009/0256947 A1 * | 10/2009 | Ciurea .................. | G06F 3/0488 348/333.12 |
| 2010/0063992 A1 * | 3/2010 | Ma ........................ | G06T 15/005 709/203 |
| 2010/0091104 A1 | 4/2010 | Sprigle et al. | |
| 2010/0286489 A1 | 11/2010 | Hartwell | |

(Continued)

OTHER PUBLICATIONS

Tarallo et al., Processing of Digital Images of Cutaneous Ulcers Through Artificial Neural Networks, Brazilian Symposium on Computer Graphics and Image Processing, 20, Oct. 7-10, 2007.*

(Continued)

*Primary Examiner* — Bo Joseph Peng
(74) *Attorney, Agent, or Firm* — W&C IP

(57) ABSTRACT

A smart phone is used to accomplish measurement of a wound surface area, when at least one flat marker device, which is a predefined reference, is placed near the wound and photographed by a smart phone.

1 Claim, 6 Drawing Sheets

(56) References Cited

U.S. PATENT DOCUMENTS

| | | | |
|---|---|---|---|
| 2011/0124987 A1 | 5/2011 | Papazoglou | |
| 2011/0177025 A1 | 7/2011 | Thanos | |
| 2012/0035469 A1 | 2/2012 | Whelan et al. | |
| 2012/0259230 A1* | 10/2012 | Riley | A61B 5/1072 |
| | | | 600/477 |

OTHER PUBLICATIONS

Suzuki et al., Estimating Object Region from Local Contour Configuration, 1st International Workshop on Visual Scene Understanding, 2009.*
TOFEL, "How to measure anything with a camera and software", https://gigaom.com/2007/02/06/how_to_measure_/, Web.
RulerPhone, http://benkamens.com/rulerphone/, 2008, Web.
Yi et al., "Quantitative wound healing measurement and monitoring system based on an innovative 3D imaging system", SPIE Proceedings, Mar. 2, 2011, vol. 7964, Abstract.
Mei, "Watershed Algorithm", Research Services Branch, National Institutes of Health, Dec. 15, 2003, Web.
"Motic Software", DC Imaging, LLC, Retrieved Oct. 11, 2012, Web.
"Free wound size area measurement software tool", Klonk Image Measurement, Retrieved Oct. 11, 2012, Web.
"Savant Imaging: Medical Imaging Innovations & Wound Area Measurement Software", Savant Imaging, Retrieved Oct. 11, 2012, Web.

* cited by examiner

WOUND MEASUREMENT ON SMART PHONES

FIELD OF THE INVENTION

The invention relates to the medical arts, more particularly, to wound measurement.

BACKGROUND OF THE INVENTION

Medical treatment of a patient with a wound typically calls for assessment of wound sizes, repeated over time to provide an indication of the patient's progress. However, existing methods of wound size assessment suffer from various disadvantages and inadequacies.

Conventionally, a medical professional's assessment of wound size has involved placement of a ruler near the wound. However, when so using a ruler, often there is not a flat surface and error is thereby added. A further complication is that a wound tends to be irregularly shaped, multicolored, and not susceptible of having its perimeter automatically defined. A further aspect is that what is used needs to be sterile.

SUMMARY OF THE INVENTION

In a preferred embodiment, the invention provides a system for measuring a wound of a patient, comprising: (A) a set of at least one flat marker device to be placed on the patient's unwounded skin near the wound, each flat marker device having a top surface with a predefined pattern; (B) a computerized system in which is stored in computer-readable form the predefined pattern and/or the known size of the flat marker device having the predefined pattern, wherein the computerized system comprises an imaging device, and wherein the computerized system performs steps comprising: capturing an image that includes the wound and the set of at least one flat marker device nearby; processing the captured image and recognizing a part of the captured image as the predefined pattern; processing the captured image and recognizing a part of the captured image as the wound; attributing a boundary to the recognized wound (such as, e.g., a step of attributing a boundary to the wound that comprises carrying out an edge-searching algorithm); after the boundary has been attributed to the wound, computing a surface area of the wound based on the known size of the flat marker device; such as, e.g., an inventive system that further comprises a screen or a display; an inventive system comprising disposable marker devices consisting of a material selected from the group consisting of paper; plastic film; and a water-resistant material; an inventive system wherein the marker device is sterile; an inventive system wherein the set of marker devices is contained within packaging that maintains the marker devices as sterile until ready for use on the patient; an inventive system wherein the computerized system is a smart phone; an inventive system wherein the imaging device is a camera in a smart phone; an inventive system wherein the computerized system performs a computing step using a watershed algorithm; an inventive system wherein the computerized system performs a computing step using image segmentation; an inventive system including a touch screen; an inventive system wherein the marker on a bottom side comprises an adhesive backing; an inventive system wherein the marker on a bottom side includes an adhesive section that only occupies a center section of the bottom side; inventive systems wherein the automated system performs watershed processing followed by contour finding; and other inventive systems.

In another preferred embodiment the invention provides a wound measurement method, comprising steps each of which is performed by an automated system of: initializing a camera including initialized buffers for image processing; obtaining captured frame data and converting to Bitmap format; converting to a gray picture and filtering out noise; edge detection processing; contour finding; and finding marker objects (such as, e.g., marker objects that are square objects; marker objects that are rectangle-shaped; etc.) and computing an average area of the marker objects; such as, e.g., inventive methods that include a step of determining whether the squares are acceptable, and if not acceptable, then repeating a step of obtaining captured frame data, and if acceptable, then proceeding to a step of determining whether a screen is touched (such as methods that include at the step of determining whether a screen is touched, if not touched, then repeating a step of obtaining captured frame data, and if touched, then proceeding to a step of obtaining a touch point); inventive methods that include using an obtained touch point as a wound sample, using neighboring location of the squares as a normal skin sample, and performing Watershed edge detection; inventive methods that include finding contours and choosing all convex contours; inventive methods that include drawing a result on a scratch buffer, finding a contour that encloses all other contours, and using the found contour as a boundary of the wound; inventive methods that include computing an area of the wound, comparing the computed area to an average area of the squares, and obtaining an absolute wound area measurement; inventive methods that include displaying the absolute wound area measurement as a displayed result; inventive methods wherein the camera is contained within a smart phone; inventive methods wherein the automated system includes a display screen that is finger-paintable; inventive methods wherein the automated system performs steps of displaying a highlighted area proposed as the wound area on the display screen, followed by receiving a finger-painted command from a medical staff person whereby the displayed highlighted area is revised; inventive methods wherein the image is captured via a camera within a smart phone operated by a medical practitioner who positioned the set of markers near the wound, positioned the camera perpendicular to the wound and at a distance where the wound and the markers were visible in the screen but not extending beyond the screen, and then operated the smart phone to take the photograph; and other inventive methods.

The invention in another preferred embodiment provides a wound measurement method, comprising: positioning a set of at least two marker devices near a wound on a patient but not touching the wound; taking an image including the wound and the thus positioned set of marker devices; wherein the image is taken via a camera or imaging device; and processing the image to arrive at a computed surface area of the wound, wherein the image-processing step is performed by a smart phone or other automated device or processor; such as, e.g., inventive methods wherein the image-processing includes recognizing the marker devices in the image and further includes recognizing the wound in the image, wherein the recognizing is performed by the smart phone or other automated device or processor; and other inventive methods.

BRIEF DESCRIPTION OF FIGURES

FIG. 4 (right) represents an initial photograph of a wound that was itself photographed by the phone in FIG. 4 during development of the invention.

DETAILED DESCRIPTION OF PREFERRED EMBODIMENT OF THE INVENTION

Figure 1:
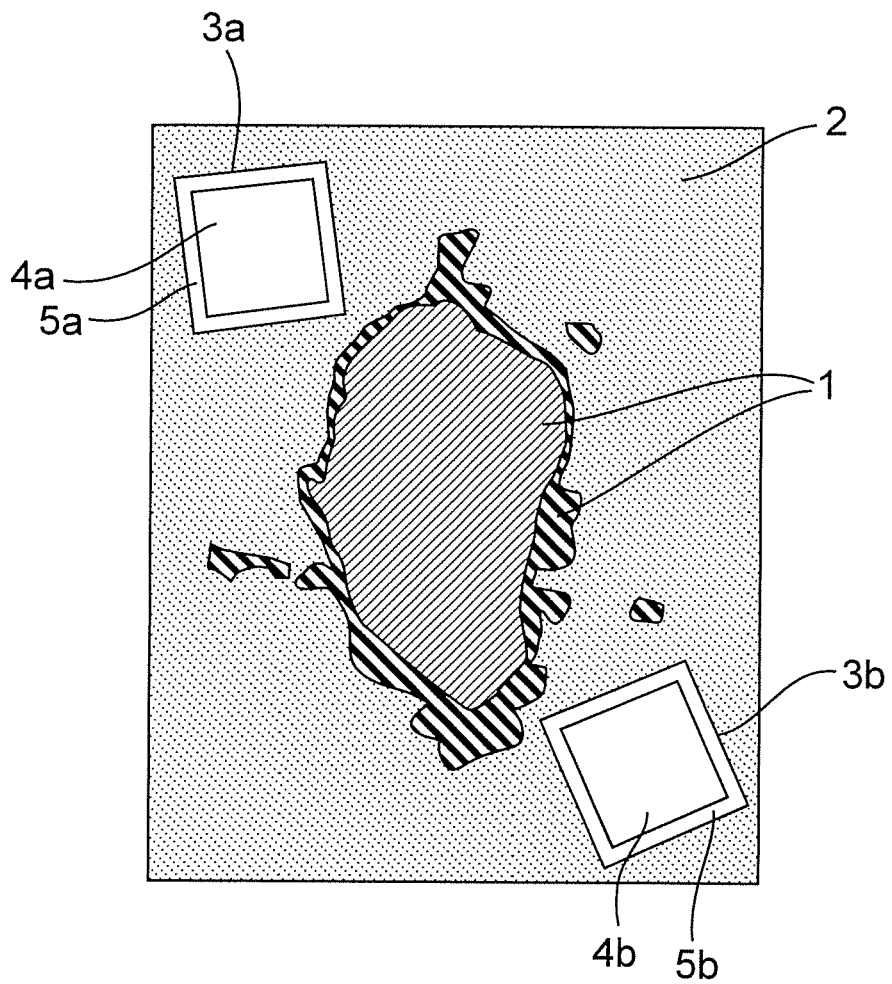
FIG. 1 is a top view of exemplary markers 3a, 3b used in practicing the invention in an embodiment, positioned near a wound 1.
Figure 2:
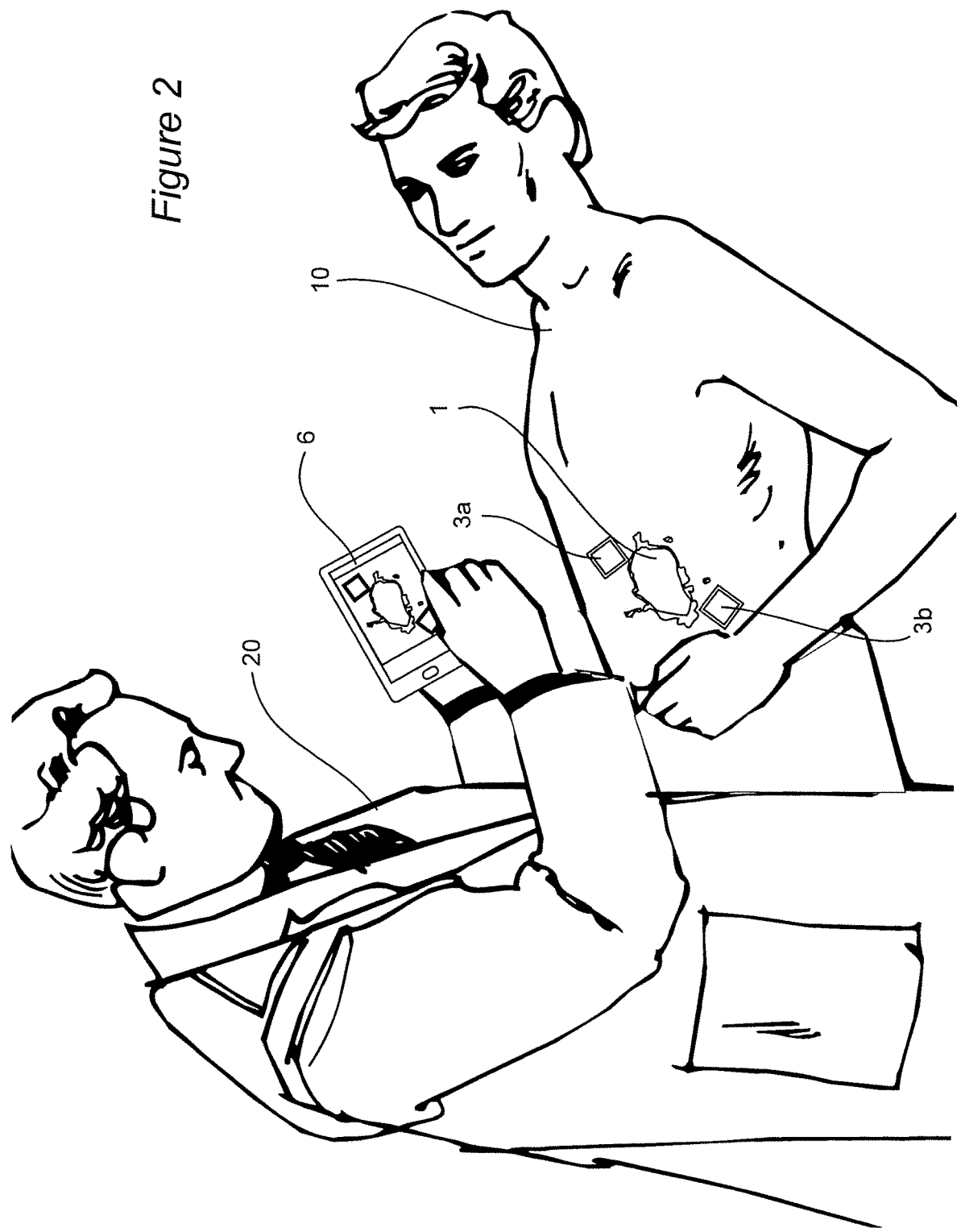
FIG. 2 is a perspective view of a medical staff person 20 and a patient 10 with a wound 1 while an inventive wound measurement method being practiced in an embodiment.

The inventive methods, systems, products and kits are useful for measuring a patient's wound, such as wound 1 in FIGS. 1-2, to give a measurement especially a surface area measurement.

Figure 3:
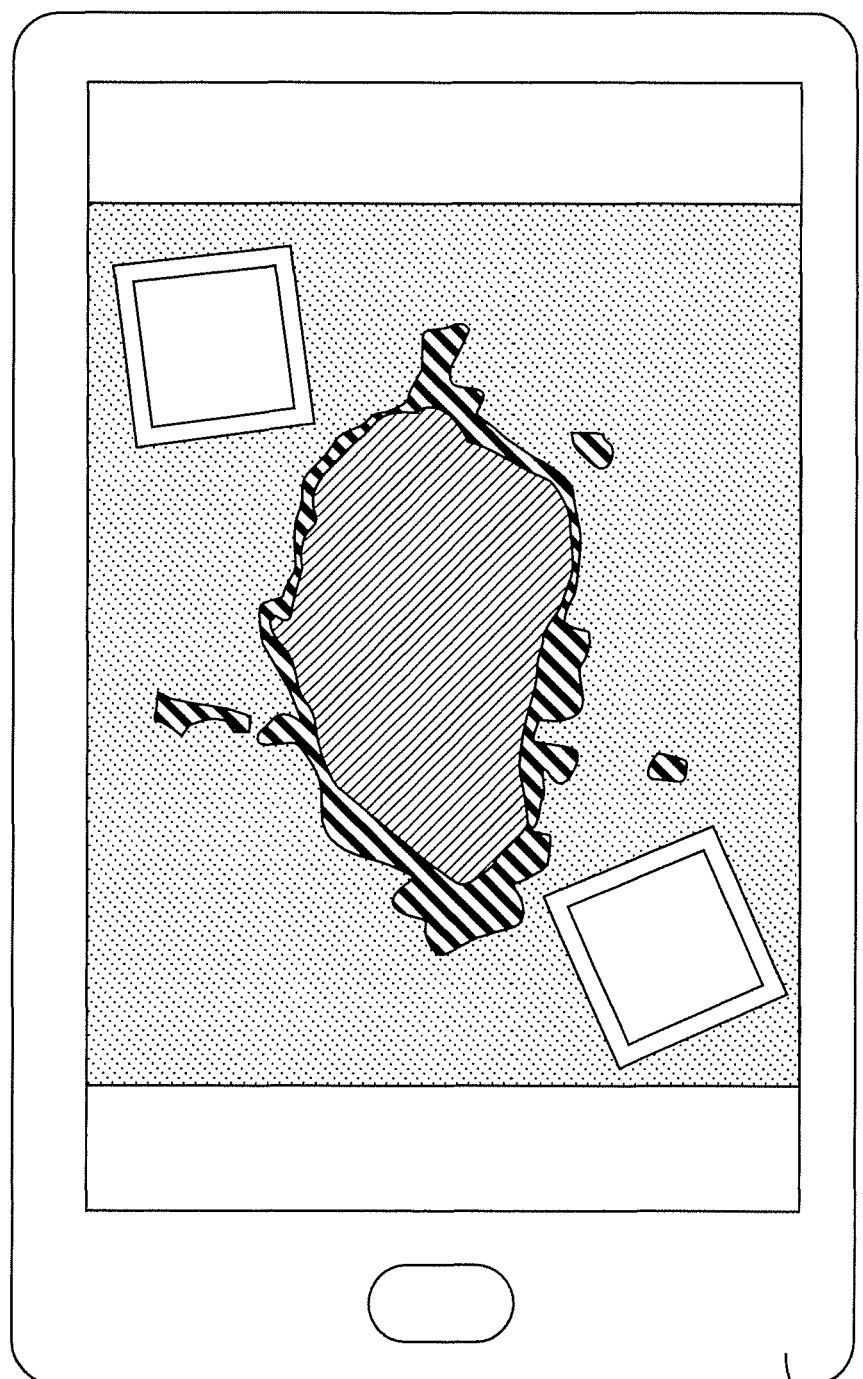
FIG. 3 is a top view of a display screen of a device 6 used in practicing an inventive wound measurement method in an embodiment.

The invention provides a set of at least one flat marker. In FIGS. 1-3, a set of two markers is shown for illustrative purposes, and in some embodiments an inventive set of markers may consist of exactly one marker. Examples of an inventive set of at least flat marker are, e.g., a set that consists of exactly one flat marker device; a set that consists of between 1 flat marker device and 6 flat marker devices; a set wherein the flat marker devices in the set are identical; etc.

A marker used in inventive systems, methods, products or kits should be readily imaged by an imaging device, preferably readily imaged by a smart phone, iPhone, etc. Examples of a preferred marker are, e.g., a flat marker device that has a top surface that consists of an interior surrounded by a contrasting exterior; a flat marker device that is square or rectangular in shape, and has a top surface that consists of an interior solid color surrounded by a contrasting exterior (such as, e.g., a top surface consisting of a white interior solid color surrounded by a black contrasting exterior); etc.

Preferred examples of a size of a marker used in the invention, are, e.g., that the marker has a surface area of at least one square inch; that the marker has a surface area of exactly one square inch; etc. The preferred size of the marker is one square inch, because, while a bigger marker tends to improve accuracy, if a bigger marker is used, there might not be enough room. For European usage, a marker size of $_2$ square cm might be preferred.

An inventive wound measurement method is begun by placing (such as placing performed by medical personnel) a set of at least one marker near a wound, such as placing markers 3a, 3b on unwounded skin 2 near wound 1.

Markers 3a, 3b have interior sections 4a, 4b and contrast rims 5a, 5b. A preferred example of a marker is a white-colored interior and a black contrast rim. Another example of a marker is a black interior and a light contrast rim.

Examples of a shape for a marker used in the invention are, e.g., a square shape, a rectangle shape, etc. In FIG. 1, markers 3a, 3b are depicted as square, which is a preferred shape for the markers.

After the markers 3a, 3b are placed on the patient 10 near the wound 1, a medical professional 20 (such as a doctor, nurse, etc.) positions device 6 (such as, e.g., a smart phone, an iPhone, etc.) over the wound 1 and after the wound 1 is positioned in the screen of the device 6, takes a photo.

A minimum number of markers to practice the invention is one marker. Using more than six markers to practice the invention would not be preferred. The reason to use more than one marker when practicing the invention is to better handle a situation in which the camera is not straight up from the area being imaged. Having more than one marker reduces error, by taking an average.

For the marker to be flat, and to be kept flat when positioned on the patient's skin, is preferred, to reduce error. A marker that conforms to the contours of the patient and loses its flatness tends to contribute to measurement error.

Preferably the marker is constructed of a material that resists curling-up. As a material for constructing the marker, a synthetic material that does not absorb water is preferred, so that the marker resists curling-up.

When constructing a marker, an adhesive backing section on a marker is preferred. When an adhesive backing is included on a marker, preferably the adhesive backing is included only at a center section of the marker.

For the user (such as the doctor or nurse) photographing the wound and the set of markers to position the camera straight up (perpendicular) with respect to the wound is preferred. The medical professional holding the camera positions the camera as close as possible to the wound being imaged without losing the wound and the marker(s) off the screen.

When writing an application to be loaded on a device for use in practicing the invention, preferably image processing used for practicing in the invention includes performance of an image segmentation method by a processor, computer, or other machine. A preferred example of an image segmentation method for use in practicing the invention is an image segmentation method that comprises computing according to a watershed algorithm. Imaging segmentation using a watershed algorithm is a method previously used by others to segment tissue such as segmenting cancer and non-cancerous tissue to get an edge. A watershed method is preferred for use in practicing the invention, because a wound tends to be multi-color, without obvious grey level, and in such a situation, a watershed method works.

After watershed processing, preferably contour-finding processing is performed.

A preferred device onto which an application is loaded, for use practicing the invention, is, e.g., a smart phone with a touch screen.

Preferably a finger painting application loaded on a device (such as, e.g., a smart phone, etc.) is used for practicing the invention.

The place of practicing inventive methods is not particularly limited, and includes, e.g., a hospital setting, at a patient's home, etc. For example, at a patient's home an image of a wound may be taken using a device, which then emails the image included in a PDF file to a doctor or other medical professional.

In the invention, preferably an image of a patient's wound only resides in RAM and is not otherwise saved, for patient privacy.

The invention may be further appreciated with reference to the following examples, without the invention being limited thereto.

EXAMPLE 1

The inventor constructed an app that runs on iPhone, Android phone and Windows phone platforms with an on board camera. A user is provided with an easy method to access the area of a 2D object with the captured object image and a reference marker.

The reference can be a ruler, in this case the user uses functions of the app to mark the length of the ruler, to thus obtain the calibration/scale data for the 2D object at the same distance.

The app also has automatic recognition capabilities towards markers of a certain shape (e.g., square). In this case, the calibration/scale data are obtained whenever such a marker is within the view of the camera.

The of-interest 2D object inside the camera view can be segmented from the background with finger painting/erasing on the smart phone's touch screen. Once done, the area measurement of the object can be derived from the scale data and the size of the painted area.

The app also provides semi-automatic segmentation to separate the object from the background. The user can tap the object on the screen and the app uses the tapping point as an example to find areas with the same imaging characteristics and mark them accordingly. For a regular wound surface which usually has similar color and visible edge the app will mark the whole wound area until the edge.

The user can lay more than one marker—usually around the wound area, the app will average the markers' scale, which is a good way to reduce the error caused by off axis (i.e., camera lens axis not perpendicular to the wound surface).

Example 1A

Figure 5:
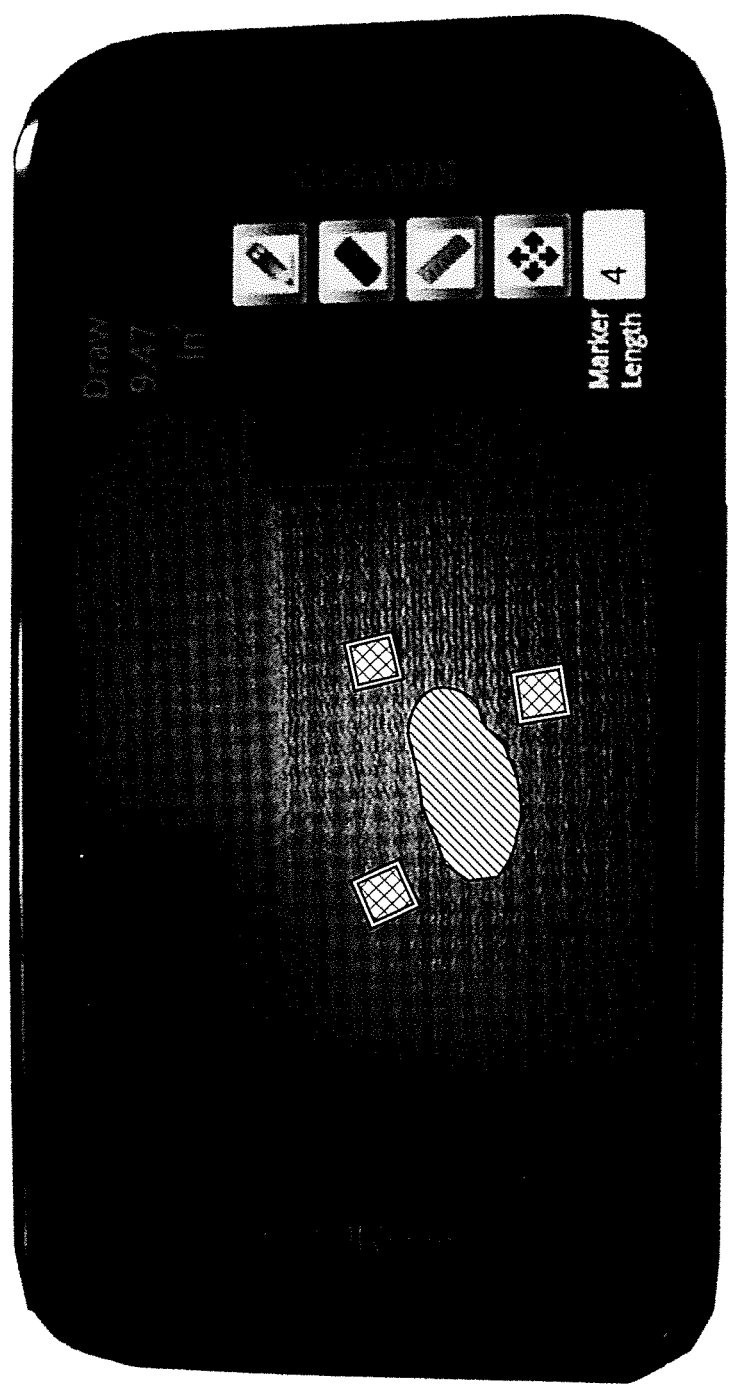
FIG. 5 was prepared from a photographic top view of a display screen of a phone device running an application according to the invention.

The inventor performed experimentation with an app that he had created and loaded onto a T-Mobile phone. Three flat, square, black-colored markers were placed on a surface around a to-be-measured test surface area. The phone (with the app created by the inventor thereon) was used to take a photograph of the three black markers, and the device processed the photographed images of the three markers and the to-be-measured test surface area. On the screen, each square black marker is outlined in pink. The app green-highlighted the to-be-measured test surface area, computed its surface area, and displayed its computed surface area as 9.47 in$^2$ on the screen. The screen was photographed, and is represented by FIG. 5 (in which cross-hatching was substituted in some areas of the photograph, for better reproducibility).

Example 1B

The inventor performed experimentation with an app that he had created and loaded onto a T-Mobile phone. Two flat, square markers were placed on a photograph of a wound having a predominantly yellow-colored section and also some red sections. Each marker had a white interior with purple-lavender-colored trim. The phone was positioned by the user so as to image the photograph of the wound, and the app computed a surface area of the wound and displayed a result on screen of 3.44 in × in.

Example 1C

Figure 4:
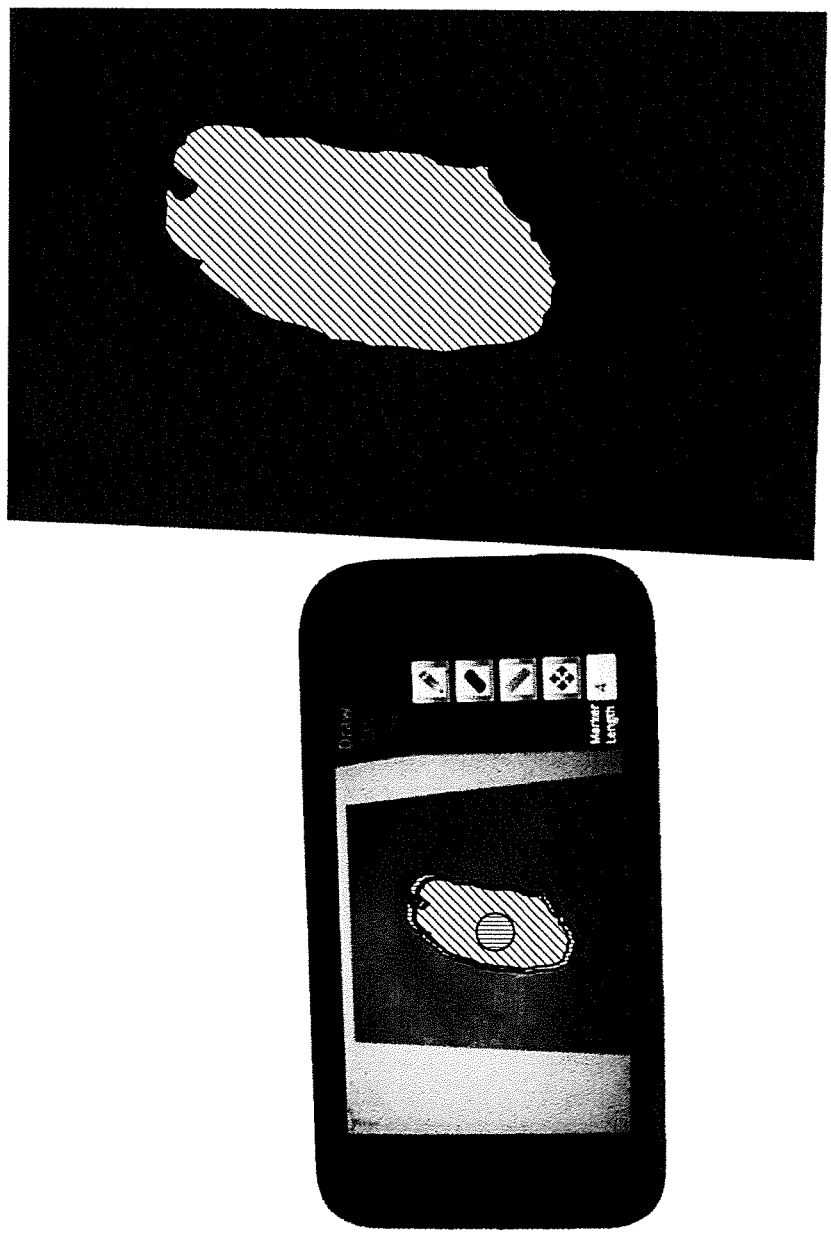
FIG. 4 (left) was prepared from a photographic top view of a display screen of a phone device running an application according to the invention.

The inventor performed experimentation with an app that he had created and loaded onto a T-Mobile phone. A red wound area poorly defined against a red background area was the subject of the experimentation. The user used the phone, and the phone captured an image. The app displayed, in green color, a proposed perimeter of the wound, and also displayed, in green color, a large circular dot, to communicate to the user what area of the image would be defined as being the wound and included when surface area was computed. The screen was photographed, and is represented by FIG. 4 (in which cross-hatching was substituted in some areas of the photograph, for better reproducibility).

Example 2

Figure 6:
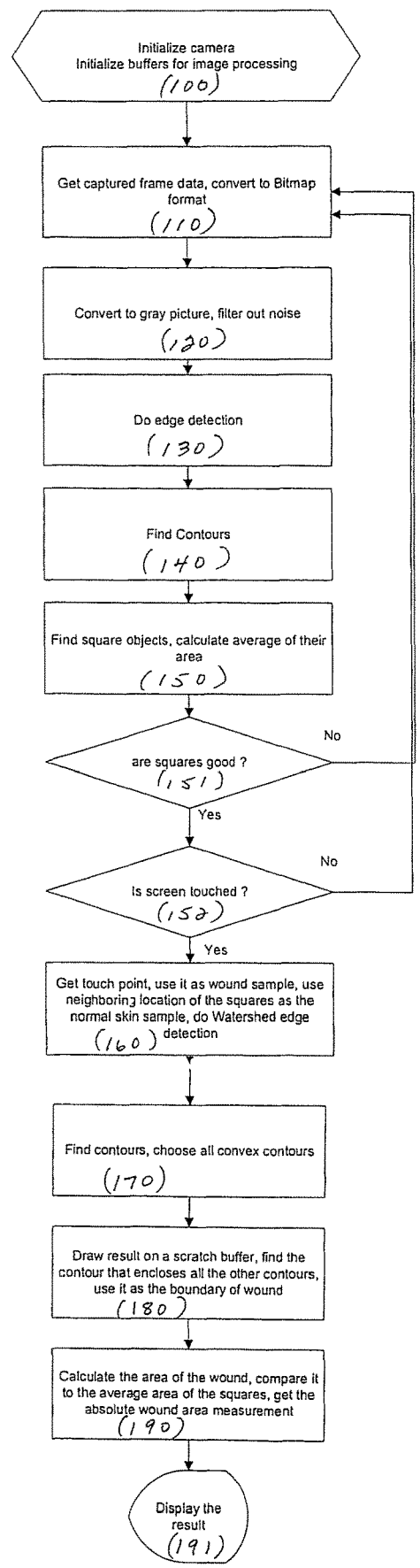
FIG. 6 is a process flow diagram of steps performed by a computer in an inventive embodiment.

In this inventive example, which may be further appreciated with reference to FIG. 6, a computer, a processor, an automated device, a machine, or a combination thereof, performs steps as follows:
  a step 100 of initializing a camera (such as a camera of a device 6) and initializing buffers for image processing; followed by
  a step 110 of getting captured frame data, and converting to Bitmap format; followed by
  a step 120 of converting to grey picture, and filtering out noise; followed by
  a step 130 of performing edge detection; followed by
  a step 140 of finding contours; followed by
  a step 150 of finding square objects, and calculating an average of their area; followed by determining 151 whether the squares are good, and if NO, then returning to step 110, and if YES, determining 152 whether the screen is touched, and if NO, then returning to step 110, and if YES, then proceeding to
  a step 160 of getting a touch point, using the obtained touch point as a wound sample, using a neighboring location of the squares as the normal skin sample, and performing Watershed edge detection; followed by
  a step 170 of finding contours, and choosing all convex contours; followed by
  a step 180 of drawing the result on a scratch buffer, finding the contour that encloses all the other contours, and using it as the boundary of the wound; followed by
  a step 190 of calculating the area of the wound, comparing it to the average area of the squares, and getting the absolute wound area measurement; followed by
  a step 191 of displaying the result (such as displaying a computed numerical quantity that is a wound surface area onto a display screen of device 6).

While the invention has been described in terms of a preferred embodiment, those skilled in the art will recognize that the invention can be practiced with modification within the spirit and scope of the appended claims.

What I claim as my invention is:

1. An absolute wound area measurement method, comprising steps, each of which is performed by a phone comprising (a) a display screen that is a touch screen and (b) an on-board camera, wherein the camera comprises initialized buffers for image processing; the steps comprising:
  obtaining captured frame data of a wound and converting to a gray picture, wherein the data-obtaining and converting are performed by the phone;
  detecting edges by watershed edge detection, performed by the phone on the gray picture;
  selecting a contour, comprising
    finding contours, performed by the phone on the gray picture,
    choosing all convex contours from the found contours,
    finding a contour from among all the convex contours that encloses all the other found contours, and
    using the found contour as a boundary of the wound;
  displaying a highlighted area proposed by the phone as the wound area on the display screen, wherein the highlighted area communicates what area of the gray picture is defined as being the wound and to include when a surface area is computed; followed by
determining whether the display screen is touched, and if yes,
 obtaining a touch point where the display screen is touched,
 using the obtained touch point as a wound sample to include in the highlighted area;
displaying, performed by the phone, an absolute wound area measurement computed by the phone based on the highlighted area, as a displayed result.

\* \* \* \* \*